(12) United States Patent
Reichle et al.

(10) Patent No.: US 9,212,111 B2
(45) Date of Patent: Dec. 15, 2015

(54) PROCESS FOR MANUFACTURING HALOARYL COMPOUNDS FROM MIXTURES OF ISOMERS OF DIHALODIARYLSULFONE

(71) Applicant: SOLVAY SPECIALTY POLYMERS USA, LLC., Alpharetta, GA (US)

(72) Inventors: Walter Reichle, Warren, NJ (US); Olivier Vidberg, Pace (FR); Nicholas Almeter, Augusta, GA (US); Chantal Louis, Alpharetta, GA (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 0 days.

(21) Appl. No.: 14/365,507

(22) PCT Filed: Dec. 11, 2012

(86) PCT No.: PCT/EP2012/075013
§ 371 (c)(1),
(2) Date: Jun. 13, 2014

(87) PCT Pub. No.: WO2013/087594
PCT Pub. Date: Jun. 20, 2013

(65) Prior Publication Data
US 2014/0323765 A1    Oct. 30, 2014

Related U.S. Application Data

(60) Provisional application No. 61/576,245, filed on Dec. 15, 2011.

(30) Foreign Application Priority Data

Mar. 9, 2012 (EP) .................................. 12158894

(51) Int. Cl.
| | | |
|---|---|---|
| C07C 17/361 | (2006.01) | |
| C07C 315/00 | (2006.01) | |
| C07C 303/02 | (2006.01) | |
| C07C 303/06 | (2006.01) | |
| C07C 17/35 | (2006.01) | |
| C07C 25/06 | (2006.01) | |
| C07C 25/08 | (2006.01) | |

(52) U.S. Cl.
CPC ............... *C07C 17/361* (2013.01); *C07C 17/35* (2013.01); *C07C 25/06* (2013.01); *C07C 25/08* (2013.01); *C07C 303/02* (2013.01); *C07C 303/06* (2013.01); *C07C 315/00* (2013.01)

(58) Field of Classification Search
CPC ...... C07C 17/361; C07C 17/35; C07C 25/06; C07C 25/08; C07C 315/00
USPC ............................................. 568/34; 570/201
See application file for complete search history.

(56) References Cited

U.S. PATENT DOCUMENTS

| | | |
|---|---|---|
| 2,511,166 A | 6/1950 | Manske |
| 3,855,312 A | 12/1974 | Horner |
| 4,983,773 A | 1/1991 | Stumpp et al. |
| 2011/0218357 A1 | 9/2011 | Deck et al. |

OTHER PUBLICATIONS

Bosscher, J. K. and Cerfontain H., "Aromatic sulfonation 20: The sulfonation of some chlorobenzenes with sulfur trioxide in nitromethane as solvent", Recueil des Travaux Chimiques des Pays-Bas, 1968, vol. 87(8), p. 873-887—doi: 10.1002/recl.19680870803.

*Primary Examiner* — Porfirio Nazario Gonzalez

(57) ABSTRACT

A process for the manufacture of a haloaryl compound which comprises contacting a mixture of dihalodiarylsulfone isomers [mixture (M)] with sulfuric acid to provide a mixture of haloarylsulfonic acid isomers [mixture (M1)] and reacting mixture (M1) in the presence of water. The process is independent on the manufacturing process of mixture (M) and is advantageous in that the obtained haloaryl compound can be recycled to the first step of a dihalodiarylsulfone manufacturing process.

15 Claims, No Drawings

PROCESS FOR MANUFACTURING HALOARYL COMPOUNDS FROM MIXTURES OF ISOMERS OF DIHALODIARYLSULFONE

This application is a U.S. national stage entry under 35 U.S.C. §371 of International Application No. PCT/EP2012/075013, filed Dec. 11, 2012, which claims priority to U.S. application No. 61/576245 filed on 15 Dec. 2011 and to EP 12158894.1 filed 9 Mar. 2012, the whole content of each of these applications being incorporated herein by reference for all purposes.

FIELD OF THE INVENTION

The present invention relates to a process for the manufacture of haloaryl compounds starting from mixtures of isomers of dihalodiarylsulfones and to a method of using the same for the manufacture of dihalodiarylsulfones.

BACKGROUND OF THE INVENTION 4,4'-Dichlorodiphenylsulfone, abbreviated as DCDPS, is an organic sulfone with the formula $(ClC_6H_4)_2SO_2$. It is most commonly used as a key monomer in the manufacture of sulfone polymers.

Other dihalodiarylsulfones than 4,4'-dichlorodiphenylsulfone and related derivatives are also of great industrial importance. Mention can be made, inter alia, of 4,4'-bis-(4-chlorophenylsulfonyl)biphenyl or of 4,4'-bis-(4-chlorophenylsulfonyl)terphenyl.

High purity levels are required in order to produce high quality polymers. More particularly, high isomeric purity is required; typical isomeric purity requirements are 98.4% and higher. Different processes for manufacturing dihalodiarylsulfones are known. In general, they result in different regioselectivity levels, but most of the time the intrinsic regioselectivity is lower than the final required purity. Hence, a waste stream consisting of dihalodiarylsulfone isomers is created. This waste stream contains unwanted isomers produced in the process but also some of the desired isomer lost during the purification step. The amount of this waste stream and its composition depend on the synthetic route chosen but also on the purification scheme used.

In particular, DCDPS is generally prepared by a two-step Friedel-Crafts sulfonation and sulfonylation reaction.

U.S. Pat. No. 4,983,773 discloses the synthesis of DCDPS by treating chlorobenzene with sulfuric acid at a temperature of 200-250° C., according to the following equations:

Cl-Ph+H$_2$SO$_4$→Cl-Ph-SO$_3$H+H$_2$O

Cl-Ph+Cl-Ph-SO$_3$H→Cl-Ph-SO$_2$-Ph-Cl+H$_2$O.

The reaction goes to completion in approximately 10 hours and produces a high yield of 4,4'-dichlorodiphenyl sulfone. The reaction can be carried out in the presence of boric acid or trifluoromethanesulfonic acid, which increases the DCDPS yield by reducing the formation of the 2,4'- and 3,4'-isomers. However, the use of high temperature leads to a decrease in selectivity (80-87% of the 4,4'-isomer).

U.S. Pat. No. 3,855,312 discloses a process for manufacturing 4,4'-dichlorophenylsulfone which comprises reacting chlorobenzene with sulfur trioxide in sulfuric acid to obtain a reaction mixture containing 4-chlorobenzenesulfonic acid, which is subsequently reacted with chlorobenzene at high temperature and superatmospheric pressure. The reaction product consists in a mixture containing 4,4'-dichlorophenylsulfone and its 2,4'- and 3,4'-isomers.

The formation of undesired disulfone isomers represents a loss in yield with the cost associated with the raw materials consumed to prepare these isomers. As opposed to sulfonylphenol-type of monomers, such as 4,4'-sulfonyldiphenol, dihalodiarylsulfone isomers cannot be chemically converted into the desired isomer in a simple one-step isomerization.

Therefore, there remains a need for reducing yield loss in manufacturing processes of dihalodiarylsulfones and possibly producing useful intermediates from the above-mentioned waste streams of unwanted isomers.

THE INVENTION

This need is met by a process according to the present invention, which allows to obtain a haloaryl compound by contacting a mixture of dihalodiarylsulfone isomers [mixture (M)] with sulfuric acid to provide a mixture of haloarylsulfonic acid isomers [mixture (M1)] and reacting mixture (M1) in the presence of water, as specified below.

The above process can be applied to mixtures (M) produced according to whichever manufacturing process and is advantageous in that the obtained haloaryl compound can either be recycled to the first step of a dihalodiarylsulfone manufacturing process or valorized in any other way.

DETAILED DESCRIPTION OF THE INVENTION

The present invention relates to a process for the manufacture a haloaryl compound which comprises:

a) contacting a mixture of dihalodiarylsulfone isomers [mixture (M)] with sulfuric acid to provide a mixture of haloarylsulfonic acid isomers [mixture (M1)] and b) reacting mixture (M1) in the presence of water to provide a haloaryl compound.

Any method known in the art can be followed for the obtainment of mixtures (M) to be used as starting materials. Furthermore, mixtures (M) may also be mixtures of dihalodiarylsulfone isomers wherein either the aryl moieties or the halogen atom on the aryl moieties or both can be different from one another. When such mixtures are used, the process of the invention affords a mixture of haloaryl compounds which may be submitted to a subsequent separation step. Mixture (M) may also comprise other components which do not interfere with the process, such as residual haloary compounds, residual metal salts and minor impurities; therefore, for the purposes of the present description, the expression "mixture(s) of dihalodiarylsulfone isomers" is also intended to mean "mixture(s) comprising dihalodiarylsulfone isomers".

According to a preferred embodiment, the process of the invention is a process for manufacturing a haloaryl compound of the formula (I):

wherein X is halogen selected from fluorine, chlorine, bromine and iodine and Ar is an aryl moiety of formula (II):

-continued

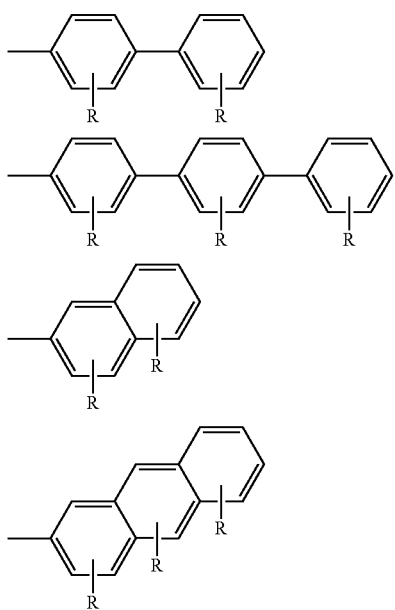

wherein R represents one or more of the groups independently selected from: hydrogen, halogen, alkyl, aryl, ether, thioether, carboxylic acid, amine and quaternary ammonium; which comprises:

a) contacting with sulfuric acid a mixture (M) of dihaloarylsulfone isomers of the formula (III):

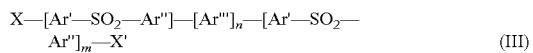 (III)

wherein:

n and m are independently 0, 1, 2, 3 or 4;

X and X', equal to or different from one another, are independently a halogen, preferably chlorine, and Ar', Ar" and Ar"', which may be the same or different from one another, represent an aryl moiety of formula (IV):

(IV)

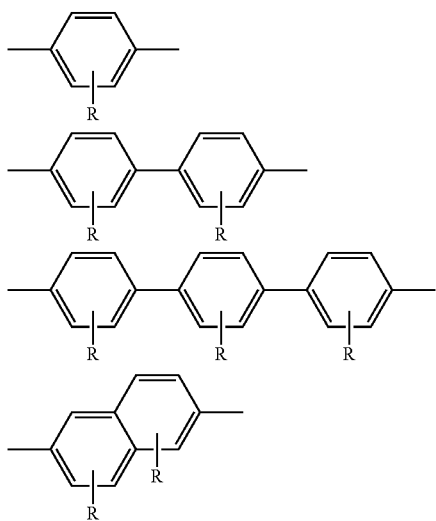

-continued

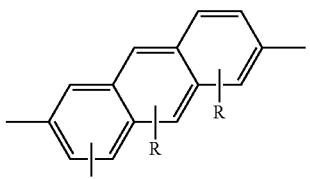

wherein R is as defined above to provide a mixture (M1) of haloaryl sulfonic acid isomers of the formula (V):

 (V)

wherein X and Ar are as defined in compound (I) and b) reacting mixture (M1) in the presence of water.

For the purposes of the present description:

"halogen" is a halogen selected from fluorine, chlorine, bromine and iodine;

"alkyl" is a saturated straight or branched hydrocarbon chain, preferably containing form 1 to 10 carbon atoms or a cyclic hydrocarbon radical, preferably containing from 3 to 10 carbon atoms;

"aryl" is an aromatic group, preferably a $C_5$-$C_{10}$ aromatic group, optionally containing one or more heteroatoms selected from N, O and S;

"ether" is an alkyloxy chain wherein alkyl is as defined above;

"thioether" is an alkylthio chain wherein alkyl is as defined above;

"carboxylic acid" is a —$CO_2H$ group or a carboxylalkylene radical, wherein alkylene is a straight or branched hydrocarbon chain preferably containing from 1 to 10 carbon atoms;

"amine" is a primary, secondary or tertiary amine of formula —$(R^1)_p$—$NH_2$, —$(R^1)_p$—$NHR^2$, —$(R^1)$—$N(R^2)_2$ wherein $R^1$ and $R^2$ are independently from one another a straight or branched hydrocarbon chain, preferably containing from 1 to 10 or carbon atoms or an aryl group as defined above and p is 0 or 1;

"quaternary ammonium" is a quaternary ammonium salt of formula —$(R^1)_p$—$N(R^2)_3^{(+)}$ wherein $R^1$, and $R^2$ and p are as defined above.

In the above formula X is preferably chlorine, while R is preferably selected from hydrogen and halogen; more preferably, X is chlorine and R is hydrogen.

More preferably, the process of the invention is a process for manufacturing a haloaryl compound X—Ar (I) as defined above, wherein Ar is a group of formula:

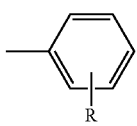

starting from a mixture (M) of dihalodiarylsulfone isomers of formula (III) as defined above wherein n=m=0 and Ar' and Ar" are the same and they are both groups of formula:

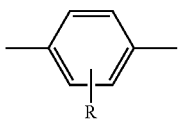

wherein X and R are defined above. Most preferably, X is chlorine and R is hydrogen, thereby obtaining chlorobenzene.

In this preferred process, mixture (M) is typically a mixture of 4,4'-, 2,4'- and 3,4'-dihalodiarylsulfones; for the manufacture of chlorobenzene, mixture (M) is a mixture of 4,4'-, 2,4'- and 3,4'-dichlorodiphenylsulfones which can be prepared, for example, according to U.S. Pat. No. 4,983,773 or according to U.S. Pat. No. 3,855,312.

Typically, step a) is carried out with an excess of concentrated sulfuric acid ($H_2SO_4$) at high temperature, typically from 200 to 260° C., preferably from 230 to 260° C. For the purposes of the present description, the expression "concentrated $H_2SO_4$" denotes a water solution of $H_2SO_4$ having a concentration of at least 85% wt, preferably ranging from 85 to 98%, more preferably from 89 to 95%, most preferably from 90 to 93%. Residence time of step a) ranges from 2 minutes to 2 hours, preferably from 5 minutes to 1 hour. The mixing of concentrated sulfuric acid with the mixture (M) can be accomplished either by adding the sulfuric acid to the mixture (M) or, more preferably, by adding the mixture (M) to the sulfuric acid.

The molar ratio between sulfuric acid and mixture (M) typically ranges from 3 and 15, preferably 4 to 10, more preferably 5 to 8.

Step a) can be conveniently carried out under a low flow of nitrogen or superheated steam in order to help the removal of any haloaryl compounds which may have formed. For the purposes of the present description, the expression "superheated steam" means steam produced by superheating deionized water to a temperature between 100 and 260° C. Additives used in industrial steam production such as corrosion inhibitors, pH control agents, etc. can be added to the steam. Preferably the steam used in step a) or b) does not contain additives; the expression "low flow" means a nitrogen flow rate typically ranging from 8 to 100 mL/mol (M) min, wherein mL denotes mL of gas at 1 atm, 0° C., preferably of about 50 mL/mol (M) min and a superheated steam flow typically ranging from 0.010 to 0.100 g/mol (M) min, preferably ranging from 0.025 to 0.050 g/mol (M) min.

Step a) can also be conveniently carried out in the presence of a soluble or non soluble acid catalyst. Examples of soluble acid catalysts are hydrochloric acid, phosphoric acid and trifluoromethanesulfonic acid, while examples of heterogeneous catalysts are zeolites and sulfated zirconia.

Furthermore, step a) can be conveniently carried out in the presence of an alkali metal salt, in order to limit reverse reaction of mixture (M1) to mixture (M). Examples of suitable alkali metal salt are sodium sulfate, sodium phosphate, sodium trifluoromethanesulfonate; sodium sulfate is preferred. The concentration of the salt present in the sulfuric acid in step a) can range from 0.1 to 10,000 ppm by weight of sulfuric acid.

Depending on the concentration of sulfuric acid, the molar ratio of sulfuric acid and mixture (M) and the reaction temperature, step a) can take place in a few minutes or in several hours. For example, when step a) is carried out on a mixture (M) of 4,4'-, 2,4'- and 3,4'-dichlorodiphenylsulfones at 260° C. with 91-95% $H_2SO_4$ at a molar ratio between acid and mixture (M) of 6, more than 85% conversion to mixture (M1) is achieved in 10 to 50 minutes.

Step b) is usually accomplished by hydrolysis at high temperature; typically, step b) is carried out by injecting superheated steam into the reaction mixture from step a) at a flow rate higher than that optionally used in step a). In step b), superheated steam is typically injected at a flow rate of ranging from 1.0 to 10.0 g/mol (M) min; preferably the flow rate is ranging from 2.0 to 8.0 g/mol (M) min, most preferably from 2.5 to 4.0 g/mol (M) min.

The injection of steam is carried out in a way to ensure proper contact with the reaction mixture. Typically, a sparging tube or dip tube is used to inject the steam at the bottom of the reaction vessel.

Step b) is typically operated at 170 to 260° C., more preferably between 200 and 250° C., most preferably between 225 and 245° C. The temperature at which step b) is carried out can be the same or different from the temperature at which step a) is carried out.

Step b) is typically carried out for 30 minutes to 30 hours, preferably from 1 to 15 hours, more preferably from 2 to 10 hours.

Steps a) and b) can be carried out either simultaneously or subsequently. When they are carried out subsequently, they are typically carried out "one-pot", i.e. without isolating mixture (M1), and the transition from step a) to step b) is done by starting injection or increasing the flow of superheated steam into the reaction vessel containing mixture (M1) and, if needed, adjusting the reaction temperature for step b).

When mixture (M) contains a low amount of 3,4'-dihalodiarylsulfone isomer, which is the most difficult to cleave, the conditions of step a) can be adjusted in such a way as to convert more than 80% of the 4,4'- and 2,4'-isomers and to leave the 3,4'-isomer unreacted. These conditions could involve shorter residence time, lower $H_2SO_4$ concentration and excess and/or lower temperature. Mixture (M1) thereby obtained could be subjected to step b) at temperatures lower than 200° C., which would allow to convert o- and p-haloarylsulfonic acids (IV) into the corresponding haloarylsulfonic acid. The lower temperature of this step would allow saving production costs; in particular, it would allow simplifying the choice of equipment, in particular material of construction. As far as equipment is concerned, it must be selected in such a way as to withstand harsh conditions, in particular is must be resistant to high temperature, pressure and to corrosion. Examples of suitable materials of construction compatible with the above-illustrated reaction conditions are glass, such as Pfaudler® glass Ultra-Glas™ 6500, Pfaudler® glass Glasteel® 9100, Pfaudler® glass Nucerite 7200, silicon carbide with reduced content of metallic silicon (preferably lower than 12% wt), such as Hexoloy® silicon carbide, graphite impregnated with phenolic compounds or with no impregnation, such as Graphilor® XBS graphite and Graphilor® XC graphite, tantalum, perfluorinated polymers such as polytetrafluoroethylene (PTFE) and copolymers of tetrafluoroethylene and perfluoroalkoxyethylene (PFA). In the vapor phase, zirconium can also be used.

The haloaryl compound of formula (I) manufactured according to the process of the invention can be conveniently recycled to the manufacture of dihalodiarylsulfones of formula (III) above or of other dihalodiarylsulfones compounds. The haloaryl compound is generally of good purity. The main impurities are acids, such as sulfur dioxide, sulfuric acid and haloarylsulfonic acids. These impurities can be removed by treatment with a caustic solution. Other, non acidic impurities, are usually entrained dihalodiarylsulfone isomers (M) and their thermal degradation products. If necessary, the haloaryl compound of formula (I) can be purified before use in order to remove any impurities; purification can be accomplished, for instance, by treatment with caustic acid solution followed by distillation.

At the end of the process, the sulfuric acid typically contains water and very low levels of organic compounds. The sulfuric acid can be conveniently recycled to step a). Recycling of sulfuric acid is particularly advantageous when the process is carried out in glass lined reactors; indeed, the recycled sulfuric acid contains some silic acid which prevents further dissolution/corrosion of the glass. Recycling of sulfuric acid generally requires a concentration step, in which the concentration is increased from 70-85% to the concentration required for step a). The concentration step can be achieved by distilling off the extra water, under atmospheric pressure or under vacuum. In case the concentration of sulfuric acid for step a) is 91%, the recycling is simply achieved by heating the sulfuric acid to 260° C. under atmospheric pressure.

Thus, the present invention further relates to a process for manufacturing a dihalodiphenysulfone which comprises the use of a haloaryl compound manufactured according to a process comprising steps a) and b) as defined above. Examples of dihalodiarylsulfones are those of formula (III):

X—[Ar'—SO$_2$—Ar'']—[Ar''']$_n$—[Ar'—SO$_2$—Ar'']$_m$—X'  (III)

Wherein X, X', Ar', Ar'', Ar''', n and m are as defined above. According to a preferred embodiment, in formula (III), X and X' are both chlorine and Ar' and Ar'' are both groups of the formula:

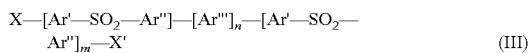

wherein R is ad defined above, preferably hydrogen, and n and m are both 0. These compounds will be herein after referred to as dihalodiarylsulfones (IIIa), represented by the following formula:

X—Ar'—SO$_2$—Ar''—X'  (IIIa)

wherein X and X' are as defined above and Ar' and Ar'', are aryl moieties of the formula:

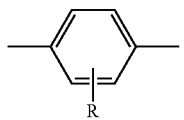

wherein R is as defined above.

A particularly preferred dihalodiarylsulfones (IIIa) is 4,4'-dichlorodiphenylsulfone.

The manufacture of dihalodiarylsulfones (IIIa) can be accomplished through a process which comprises the following steps:

a') sulfonating a haloaryl compound X—Ar (I) wherein Ar is an aryl moiety of formula:

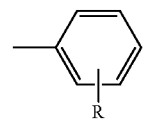

wherein X and R are as defined above to provide a mixture (M1) of haloarylsulfonic acids isomers of the formula (V):

X—Ar—SO$_3$H  (V)

wherein X is as defined above and Ar is an aryl moiety of formula:

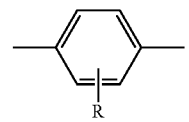

wherein R is as defined above b') reacting mixture (M1) with a haloaryl compound X—Ar (I) as defined in step a') above to provide a mixture (M) of dihalodiarylsulfones isomers complying with formula (IIIa):

c') isolating the 4,4'-dihalodiarylsulfone isomer from mixture (M);

d') subjecting mixture (M) to steps a) and b) as defined above so as to obtain a haloaryl compound X—Ar (I) as defined in step a') above and e') recycling haloaryl compound X—Ar (I) to step a') or b').

Steps a') and b') can be carried out according to any known sulfonation and sulfonylation methods for the preparation of dihalodiaryl sulfones. For example, step a') can be accomplished by treating a haloaryl compound X—Ar (I) as defined above with SO$_3$ at a temperature ranging from 40 to 85° C. and step b') can be accomplished at a temperature ranging from 200 to 250° C.

Alternatively, the manufacture of dihalodiarylsulfones (IIIa) can be accomplished through a process which comprises the following steps:

a') chlorosulfonating a haloaryl compound X—Ar (I) wherein Ar is an aryl moiety of formula:

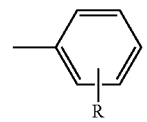

wherein X and R are as defined above to provide a mixture (M1') of haloarylsulfonyl chlorides isomers of the formula (VI):

X—Ar—SO$_2$Cl  (VI)

wherein X is as defined above and Ar is an aryl moiety of formula:

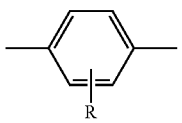

wherein R is as defined above b') reacting mixture (M1') with a haloaryl compound X—Ar (I) as defined in step a') above to provide a mixture (M) of dihalodiarylsulfones isomers complying with formula (IIIa) as defined above;

c') isolating the 4,4'-dihalodiarylsulfone isomer from mixture (M);

d') subjecting mixture (M) to steps a) and b) as defined above so as to obtain a haloaryl compound X—Ar (I) as defined in step a') above and e') recycling haloaryl compound X—Ar (I) to step a') or b'.

Step a') can be accomplished with chlorosulfonic acid at a temperature ranging from 0 to 50° C., while step b') can be accomplished at 120-190° C. in the presence of $AlCl_3$ or $FeCl_3$.

Alternatively, the manufacture of dihalodiarylsulfones (IIIa) can be accomplished through a process which comprises the following steps:

a') reacting a complex of sulfur trioxide with dialkyl sulfate with a haloaryl compound X—Ar (I) wherein Ar is an aryl moiety of formula:

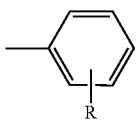

wherein X and R are as defined above to provide a mixture (M) of dihalodiarylsulfones isomers complying with formula (IIIa) as defined above;

b') isolating the 4,4'-dihalodiarylsulfone isomer from mixture (M);

d') subjecting mixture (M) to steps a) and b) as defined above so as to obtain a haloaryl compound X—Ar (I) as defined in step a') above and c') recycling haloaryl compound X—Ar (I) to step a').

Step a') can be accomplished with dimethyl sulfate at a temperature ranging from 0 to 80° C. or with diethyl sulfate at a temperature ranging from −10 to 20° C.

Other alternate manufacturing processes for the manufacture of dihalodiarylsulfones are disclosed in U.S. provisional applications 61/476,413 and 61/476,419.

Should the disclosure of any patents, patent applications, and publications which are incorporated herein by reference conflict with the description of the present application to the extent that it may render a term unclear, the present description shall take precedence.

The invention is illustrated below in greater detail by means of non-limiting examples.

EXAMPLES

Reagents

The following reagents were used to carry out the examples:

Mixture of dihalodiarylsulfones (III): mixture of dichlorodiphenylsulfone isomers byproduct in the crystallization in monochlorobenzene of a crude reaction mixture according to U.S. Pat. No. 3,855,312;

Mixture of chlorobenzenesulfonic acid, dichlorodiphenylsulfone, $H_2SO_4$ and MCB was obtained by reaction between MCB and sulfur trioxide according to Cerfontain et al, *Recueil*, 1968, V 87, P 873-887;

Sulfuric acid was purchased from JTBaker, Analyzed grade, 95-98 wt %;

Sodium sulfate, Aldrich, ACS reagent, ≥99.0%, powder, used as received;

Methylene chloride (HPLC grade), ethanol (anhydrous, 200 proof), triethylorthoacetate (97%), diphenyl sulfoxide (96%) were purchased from Aldrich and used as received.

Analytical Method

A derivatization solution was prepared by mixing:

810.00 g, Methylene chloride, $CH_2Cl_2$ 134.00 g Triethylorthoacetate (esterification agent)

20.0000 g Ethanol 200 proof (helps the esterification)

4.0000 g Diphenyl sulfoxide (internal standard).

Each sample to analyze by GC was derivatized by treating 0.1500 g of sample with 10 mL of derivatization solution. The weights of the sample and the solution used were used for the quantitative analysis using diphenyl sulfoxide as the internal standard. Sulfuric acid is derivatized into diethylsulfate, chlorobenzensulfonic acid into ethyl chlorobenzenesulfonate.

Gas chromatographic analysis was performed on an Agilent HP6890 Gas Chromatograph, using an HP column: HP-5, 15 m×0.25 mm dia., 0.25 micron film thickness and the running conditions were:

Injector temperature 290° C.

Detector temperature (FID) 300° C.

Oven ramp: 35° C., hold for 1 minute, then to 325° C. at 15° C./minute, 10 minute hold at 325° C.

Split ratio: 60:1

Injection volume: 1 μL

Carrier gas flow (helium): 1 mL/minute.

The GC retention time for the different analytes is:

| Component | Retention time (min) |
|---|---|
| Monochlorobenzene | 4.2 |
| Diethyl sulfate ($H_2SO_4$) | 7.0 |
| Ethyl 4-chlorobenzenesulfonate | 10.5 |
| Ethyl 2-chlorobenzenesulfonate | 10.7 |
| 3,4'-dichlorodiphenylsulfone | 14.2 |
| 3,4'-dichlorodiphenylsulfone | 14.3 |
| 3,4'-dichlorodiphenylsulfone | 14.5 |

Brief Explanation of the Examples

Examples 1 through 6 are examples of step a) according to the invention and show the relative reactivity of the dichlorodiphenylsulfone isomers under different conditions and show that mixtures containing high amounts of 3,4'-dichlorodiphenylsulfone require harsher reaction conditions. Positive impact of nitrogen flow is shown in examples 1 and 2.

Examples 7 through 9 exemplify the process (steps a)+b)) according to the invention using virgin $H_2SO_4$.

Example 10 shows the improvement in monochlorobenzene (MCB) purity when $Na_2SO_4$ is added to the acid.

Example 11 exemplifies the process according to the invention in which the second step is operated at lower temperature.

Example 12 exemplifies recycling of $H_2SO_4$.

Examples 13 and 14 show that the thus produced monochlorobenzene can be used in the manufacture of dichlorodiphenylsulfone.

Example 1

95% $H_2SO_4$, 6 mol $H_2SO_4$/mol DCDPS, 260° C., no Steam Injection, no Nitrogen Flow In a 5-neck 500-mL reactor flask fitted with a glass mechanical stirrer, a thermocouple (in a glass well), a glass frit for the steam or nitrogen inlet, a heated addition funnel and a Vigreux column connected to a reflux condenser and a 1-liter collection flask, were introduced 366.32 g of 96.5 wt % $H_2SO_4$ (3.57 mol) and 98 g of water. The final concentration was 95 wt %. The acid was heated to 260° C.

172.84 g of a mixture of dichlorodiphenylsulfone isomers (0.60 mol, 49% 4,4'-isomer, 30% 2,4'-isomer, 21% 3,4'-isomer) were added to the addition funnel and heated to 200° C.

When the acid in the reaction flask had reached 260° C., the molten mixture of isomers was added in 1 minute to the acid. The reaction mixture was held at 260° C. for 20 minutes. At the end of the reaction, the conversion of the different of DCDPS isomers was measured by GC. A new DCDPS isomer (3,3'-DCDPS) was formed during the reaction and found to limit the conversion. Details are in table 1.

Example 2

95% $H_2SO_4$, 6 mol $H_2SO_4$/mol DCDPS, 260° C., no Steam Injection, with Nitrogen Flow The same procedure as for example 1 was followed except for the following modifications;

$H_2SO_4$ 95%: 366.56 g, 3.55 mol

DCDPS isomers mixture: 172.62 g, 0.60 mol

Reaction was run with nitrogen flow (30 mL/min) at 260° C. for 20 minutes.

At the end of the reaction, the conversion of the different of DCDPS isomers was measured by GC. Details are in table 1.

Example 3

91% $H_2SO_4$, 6 mol $H_2SO_4$/mol DCDPS, 260° C., no Steam Injection

The same procedure as for example 1 was followed except for the following modifications;

$H_2SO_4$ 91%: 2581.34 g, 23.95 mol

DCDPS isomers mixture: 1149.0 g, 4.00 mol

Reaction was run with nitrogen flow (30 mL/min) at 260° C. for 20 minutes.

At the end of the reaction, the conversion of the different of DCDPS isomers was measured by GC. Details are in table 1.

Example 4

91% $H_2SO_4$, 3 mol $H_2SO_4$/mol DCDPS, 260° C., no Steam Injection

The same procedure as for example 1 was followed except for the following modifications;

$H_2SO_4$ 91%: 1902.21 g, 17.66 mol

DCDPS isomers mixture: 1682.00 g, 5.86 mol

Reaction was run with nitrogen flow (30 mL/min) at 260° C. for 20 minutes.

At the end of the reaction, the conversion of the different of DCDPS isomers was measured by GC. Details are in table 1.

Example 5

91% $H_2SO_4$, 6 mol $H_2SO_4$/mol DCDPS, 245° C., no Steam Injection

The same procedure as for example 1 was followed except for the following modifications;

$H_2SO_4$ 91%: 2597.28 g, 24.10 mol

DCDPS isomers mixture: 1148.0 g, 4.00 mol

Reaction was run with nitrogen flow (30 mL/min) at 245° C. for 20 minutes.

At the end of the reaction, the conversion of the different of DCDPS isomers was measured by GC. Details are in table 1.

Example 6

91% $H_2SO_4$, 3 mol $H_2SO_4$/mol DCDPS, 245° C., no Steam Injection

The same procedure as for example 1 was followed except for the following modifications; $H_2SO_4$ 91%: 1893.00 g, 17.52 mol DCDPS isomers mixture: 1682.00 g, 5.86 mol Reaction was run with nitrogen flow (30 mL/min) at 245° C. for 20 minutes.

At the end of the reaction, the conversion of the different of DCDPS isomers was measured by GC. Details are in table 1.

Example 7

91% $H_2SO_4$, 3 mol $H_2SO_4$/mol DCDPS, 260° C.

In a 5-neck 3-liter reactor flask fitted with a glass mechanical stirrer, a thermocouple (in a glass well), a glass frit for the steam or nitrogen inlet, a heated addition funnel and a Vigreux column connected to a reflux condenser and a 4-liter collection flask, were introduced 1793 g of 96 wt % $H_2SO_4$ (17.55 mol) and 98 g of water. The final concentration was 91 wt %. The acid was heated to 260° C. Nitrogen was fed to the reaction flask at 30 mL/min.

1682 g of a mixture of dichlorodiphenylsulfone isomers (5.86 mol, 49% 4,4'-isomer, 30% 2,4'-isomer, 21% 3,4'-isomer) were added to the addition funnel and heated to 200° C.

When the acid in the reaction flask had reached 260° C., the molten mixture of isomers was added in 1 minute to the acid. After 30 minutes, 80% of DCDPS had been converted. The nitrogen flow to the flask was interrupted and superheated steam (produced by superheating deionized water to reach a temperature of 170° C.) was fed into the reaction flask via the glass frit at 10 g/min for 4 hours while maintaining the reaction mixture temperature at 260° C. At the end of the reaction, 99.9% of the DCDPS had been converted and 1008 g of monochlorobenzene (8.96 mol, 76% yield) had been collected along with 2057 g of water. The purity of the thus formed MCB was 99.6% pure by GC. Impurities are detailed in table 2. The $H_2SO_4$ concentration was 85 wt %.

Example 8

91% $H_2SO_4$, 4 mol $H_2SO_4$/mol DCDPS, 260° C. and 245° C.

The same procedure as for example 7 was followed except for the following modifications;

$H_2SO_4$ 91%: 2091 g, 19.40 mol
DCDPS isomers mixture: 1393 g, 4.85 mol
Reaction before steam injection was run at 260° C. for 50 minutes
Reaction after steam injection was run at 245° C. for 7.5 hours.

At the end of the reaction, 100.0% of the DCDPS had been converted and 1108 g of monochlorobenzene (9.85 mol, 99% yield) had been collected along with 4218 g of water. The purity of the thus formed MCB was 98.9% pure by GC. Impurities are detailed in table 2. The $H_2SO_4$ concentration was 83 wt %.

Example 9

95% $H_2SO_4$, 6 mol $H_2SO_4$/mol DCDPS, 260° C.

The same procedure as for example 7 was followed except for the following modifications;
500 mL reaction flask
$H_2SO_4$ 95%: 557.50 g, 5.40 mol
DCDPS isomers mixture: 258.45 g, 0.90 mol
Reaction before steam injection was run at 260° C. for 10 minutes
Steam rate: 3.24 g/min
Reaction after steam injection was run at 260° C. for 4 hours.

At the end of the reaction, 99.5% of the DCDPS had been converted and 171.95 g of monochlorobenzene (1.52 mol, 83% yield) had been collected along with 401.61 g of water. The purity of the thus formed MCB was 99.4% pure by GC. Impurities are detailed in table 2. The $H_2SO_4$ concentration was 85 wt %.

Example 10

95% $H_2SO_4$, 6 mol $H_2SO_4$/mol DCDPS, 260° C., with $Na_2SO_4$

The same procedure as for example 7 was followed except for the following modifications;
500 mL reaction flask
$H_2SO_4$ 95%: 557.78 g, 5.38 mol
DCDPS isomers mixture: 258.45 g, 0.90 mol
$Na_2SO_4$: 0.80 g
Reaction before steam injection was run at 260° C. for 10 minutes
Steam rate: 3.24 g/min
Reaction after steam injection was run at 260° C. for 4 hours.

At the end of the reaction, 99.7% of the DCDPS had been converted and 155.82 g of monochlorobenzene (1.38 mol, 76% yield) had been collected along with 507.54 g of water. The purity of the thus formed MCB was 99.5% pure by GC. Impurities are detailed in table 2. The $H_2SO_4$ concentration was 84 wt %.

Example 11

91% $H_2SO_4$, 10 mol $H_2SO_4$/mol DCDPS, 260° C. then 200° C., Lower DCDPS Conversion in First Step The same procedure as for example 7 was followed except for the following modifications;
500 mL reaction flask
$H_2SO_4$ 91%: 522.13 g, 4.84 mol
DCDPS isomers mixture: 140.04 g, 0.49 mol
Reaction before steam injection was run at 260° C. for 2 minutes
Steam rate: 1.00 g/min
Reaction after steam injection was run at 200° C. for 4 hours.

When steam was first injected in the system, DCDPS had been 69% converted.

At the end of the reaction with steam, 86% of the DCDPS had been converted and 59.82 g of monochlorobenzene (0.53 mol, 57% yield) had been collected along with 142.76 g of water. The purity of the thus formed MCB was 96.2% pure by GC. Impurities are detailed in table 2. The $H_2SO_4$ concentration was 70 wt %.

Example 12

Recycling of $H_2SO_4$

At the end of the reaction of example 8, the steam injection was interrupted and the reaction mixture was heated back to 260° C. 228 g of water were collected as distillate. Nitrogen was fed to the reaction flask at 30 mL/min. 1393.00 g of molten isomers mixture (4.85 mol) were added via the addition funnel. The reaction was held at 260° C. for 50 minutes then, steam was injected in the reaction mixture at 10 g/min and the reaction temperature was lowered to 245° C. The reaction was held at 245° C. for 7 hours. At the end of the reaction, 100.0% of the DCDPS had been converted and 1207 g of monochlorobenzene (10.72 mol, 99% yield) had been collected along with 4261 g of water. The purity of the thus formed MCB was 98.9% pure by GC. Impurities are detailed in table 2. The $H_2SO_4$ concentration was 82 wt %.

Example 13

Use of MCB in Sulfonation Reaction

The MCB produced in example 8 was washed with the same volume of 0.02% aq. potassium hydroxide solution, then washed again with 3 times the same volume of deionized water. The final moisture content of the MCB was approx. 1000 ppm by weight as measured by Karl-Fisher titration.

In a dry 3-neck 250-mL round bottom flask, containing a PTFE-coated stir bar and fitted with a thermocouple, a distillation receiver allowing returning the vapors to the mixture (Barrett trap)+reflux condenser+$H_2SO_4$ scrubber, and a inlet tube connected to an oleum distillation set up and a nitrogen inlet, was introduced under nitrogen 90.06 g of MCB from example 8 neutralized as detailed above (0.80 mol).

The flask was then sealed and the mixture was heated to 75° C. under agitation. When the mixture had reached 75° C., 55.00 g of $SO_3$ vapors (0.14 mol) were slowly introduced to the reactor from an adjacent oleum distillation set up. The addition lasted 60 minutes, during which the temperature was maintained at 75° C. by applying external cooling to the reaction flask. At the end of the addition, the reaction mixture was held at 75° C. for 1 hour. At the end of the reaction, the mixture was analyzed by GC and found to contain:
61 wt % chlorobenzenesulfonic acid (0.49 mol, 67% yield, 95.7% pCBSA/4.3% oCBSA)
14 wt % DCDPS (0.07 mol, 9% yield, 90%/5.5%/3.5% 4,4'/2,4'/3,4')
9 wt $H_2SO_4$ (0.13 mol, 19% yield)
16 wt % MCB (0.19 mol).

Example 14

Use of MCB in Sulfonylation Reaction

A mixture of chlorobenzenesulfonic acid and DCDPS obtained by reaction of MCB with SO$_3$ produced was used as starting material for sulfonylation reaction. The composition of the initial mixture was:

- 67.6 wt % chlorobenzenesulfonic acid (97.3% pCBSA/ 2.7% oCBSA)
- 21.5 wt % dichlorodiphenylsulfone (85.5% 4,4'-DCDPS/ 4.7% 2,4'-DCDPS/9.7% 3,4'-DCDPS)
- 6.7 wt % H$_2$SO$_4$
- 4.2 wt % MCB.

Example 8 was repeated several times to accumulate enough MCB. The MCB thus produced was washed with the same volume of 0.02% aq. potassium hydroxide solution, then washed again with 3 times the same volume of deionized water. The final moisture content of the MCB was approx. 1000 wtppm.

In a 4-neck 500-mL reactor flask fitted with a glass mechanical stirrer, a thermocouple (in a glass well), a glass frit for MCB vapors inlet and a Vigreux column connected to a reflux condenser and a 4-liter collection flask, were introduced 370 g of the CBSA mixture (1.29 mol). The mixture was heated to 235° C.

The MCB from example 8 neutralized as detailed above was fed to the reaction flask, via the glass frit, at 23.4 g/min for 70 minutes. At the end of the reaction, the reaction mixture (429 g) was analyzed by GC and found to contain:
- 53 wt % chlorobenzenesulfonic acid (1.17 mol)
- 43 wt % DCDPS (0.65 mol, 28% yield, 84.4% 4,4'-DCDPS/6.3% 2,4'-DCDPS/9.3% 3,4'-DCDPS).

TABLE 1

| Ex | 4,4'-DCDPS conversion (mol %) | 2,4'-DCDPS conversion (mol %) | 3,4'-DCDPS conversion (mol %) | Total DCDPS conversion (mol %) | DCDPS converted into 3,3'-DCDPS (mol %) |
|---|---|---|---|---|---|
| 1 | 98 | 100 | 93 | 91 | 6.1 |
| 2 | 98 | 100 | 92 | 93 | 4.0 |
| 3 | 96 | 100 | 67 | 91 | 0.6 |
| 4 | 77 | 95 | 35 | 73 | 0.9 |
| 5 | 81 | 94 | 31 | 76 | 0.4 |
| 6 | 35 | 62 | −5* | 36 | 0.4 |

*3,4'-isomer produced by isomerization of 4,4'- and 2,4'-isomer

TABLE 2

| example | MCB purity (GC area %) | Dichlorobiphenyl (ppm) | Dichlorodiphenylsulfides (ppm) | DCDPS (ppm) | Dichlorobenzene (3 isomers) (ppm) | Chlorotoluene (3 isomers) (ppm) | SO$_2$ (ppm) | phenol and chlorophenols (ppm) |
|---|---|---|---|---|---|---|---|---|
| 7 | 99.6 | 42 | 358 | 2581 | 145 | 190 | 833 | 13 and 103 |
| 8 | 98.9 | 69 | 543 | 9819 | 44 | 121 | N/A | <5 |
| 9 | 99.4 | 0 | 1724 | 3649 | <5 | <5 | N/A | <5 |
| 10 | 99.5 | 0 | 531 | 2563 | <5 | <5 | N/A | <5 |
| 11 | 96.2 | 30 | 231 | 37630 | <5 | 139 | N/A | <5 |
| 12 | 98.9 | 89 | 784 | 11343 | <5 | 103 | N/A | <5 |

The invention claimed is:

1. A process for manufacturing a haloaryl compound comprising:
   a) contacting a mixture (M) of dihalodiarylsulfone isomers with sulfuric acid to provide a mixture (M1) of haloarylsulfonic acid isomers and
   b) reacting mixture (M1) in the presence of water to provide a haloaryl compound.

2. The process according to claim 1, wherein the haloaryl compound is according to formula (I):

wherein
X is halogen selected from fluorine, chlorine, bromine and iodine, and
Ar is an aryl moiety of formula (II):

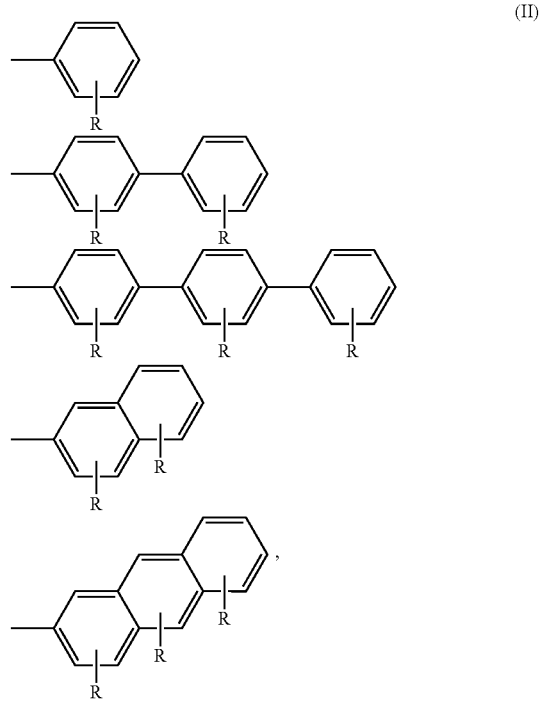

and
R is independently selected from: hydrogen, halogen, alkyl, aryl, ether, thioether, carboxylic acid, amine and quaternary ammonium, said process comprising:
a) contacting with sulfuric acid a mixture (M) of dihaloarylsulfone isomers of the formula (III):

X—[Ar'—SO$_2$—Ar"]—[Ar''']$_n$—[Ar'—SO$_2$—Ar"]$_m$—X'  (III)

wherein:

n and m are independently 0, 1, 2, 3 or 4,

X and X', which may be equal to or different from one another, are independently halogen, as defined in regard to formula (I), and Ar', Ar" and AR''', which may be the same or different from one another, represent an aryl moiety of formula (IV):

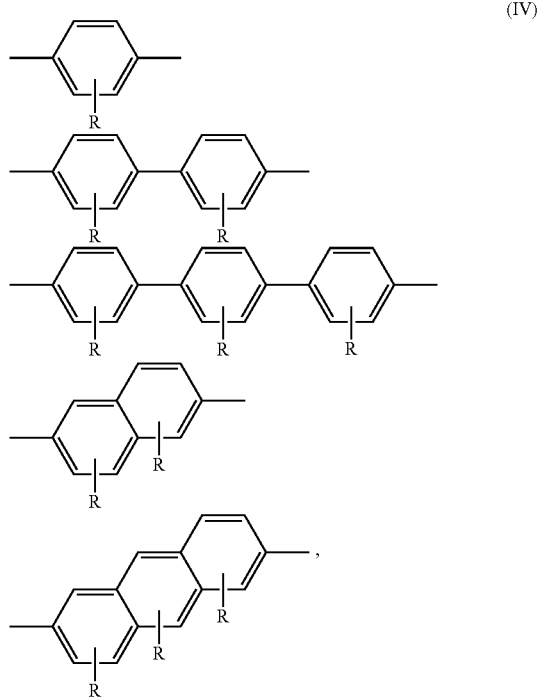

(IV)

and

R is as defined in regard to formula (I), to provide a mixture (M1) of haloaryl sulfonic acid isomers of the formula (V):

X—Ar—SO$_3$H  (V)

wherein X and Ar are as defined in regard to formula (III), and b) reacting mixture (M1) in the presence of water.

3. The process according to claim 2, wherein, in the haloaryl compound of formula (I):

Ar is an aryl moiety of formula:

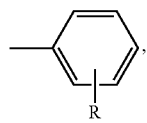

and, in the dihaloarylsulfone isomers according to formula (III):

n = m = 0,

Ar' and Ar" are the same and they are both groups of formula:

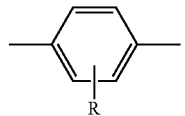

R is as defined in regard to formula (I).

4. The process of claim 3 in which mixture (M) is a mixture of 4,4'-, 2,4'- and 3,4'-dihalodiarylsulfones.

5. A process of according to claim 1, in which step a) is carried out by treatment with an excess of sulfuric acid (H$_2$SO$_4$) having a concentration of at least 85%.

6. The process according to claim 1, in which step a) is carried out at a temperature ranging from 200 to 260° C. and step b) at a temperature ranging from 170 to 260° C.

7. The process according to claim 1, in which an acid catalyst or an alkali metal salt is added in step a).

8. A process according to claim 1, in which step b) is carried out by steam-hydrolysis.

9. A process for manufacturing a dihalodiaryl sulfone, comprising:

(a) providing a mixture (M) of mixture of dihalodiarylsulfones isomers by:

(1) (i) sulfonating a haloaryl compound to provide a mixture (M1) of haloarylsulfonic acids isomers and (ii) reacting the mixture (M1) with a haloaryl compound, wherein the haloaryl compound of step (1)(i) or step (1)(ii) is made by the process of claim 1, or (2) (i) chlorosulfonating a haloaryl compound made by the process of claim 1 to provide a mixture (M1') of haloarylsulfonyl chlorides isomers, and (ii) reacting mixture (M1') with a haloaryl compound, wherein the haloaryl compound of step (2)(i) or step (2)(ii) is made by the process of claim 1, or (3) reacting a complex of sulfur trioxide and dialkyl sulfate with a haloaryl compound, wherein the haloaryl compound of step (3) is made by the process of claim 1, and (b) isolating the dihalohydrin sulfone from the mixture (M).

10. The process according to claim 9, wherein the dihalodiaryl sulfone is according to formula (III):

X—[Ar'—SO$_2$—Ar"]—[Ar''']$_n$—[Ar'—SO$_2$—Ar"]$_m$—X'  (III)

wherein

X and X', which may be equal to or different from one another, are independently halogen selected from fluorine, chlorine, bromine, and iodine, Ar', Ar" and Ar''', which may be the same or different from one another, represent an aryl moiety of formula (IV):

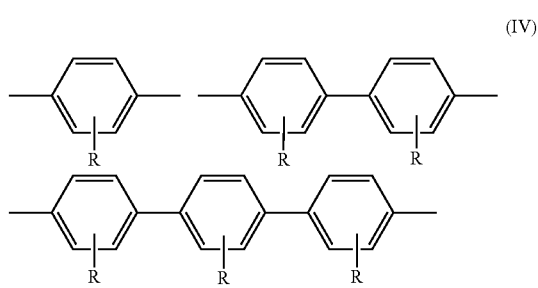

(IV)

-continued

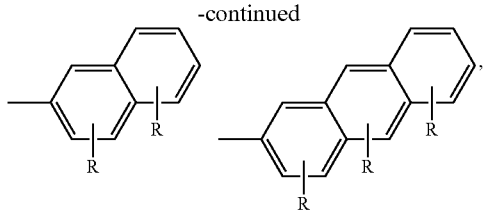

n and m are independently 0, 1, 2, 3, or 4.

11. A process for manufacturing a 4,4'-dihalodiaryl sulfone according to formula (III):

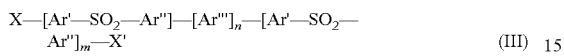 (III)

wherein in compound (III):
X and X' are independently selected from fluorine, chlorine, bromine, and iodine,
Ar' and Ar'' are both groups of the formula:

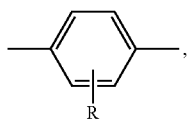

each R is independently selected from hydrogen, halogen, alkyl, aryl, ether, thioether, carboxylic acid, amine, and quaternary ammonium, and
n and m are both 0, said process comprising:
a') sulfonating a haloaryl compound according to formula (I):

X—Ar (I)

wherein:
Ar is an aryl moiety of formula:

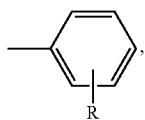

and
X and R are as defined in regard to formula (III);
to provide a mixture (M1) of haloarylsulfonic acids isomers of the formula (V):

X—Ar—SO$_3$H (V)

wherein:
Ar is an aryl moiety of formula:

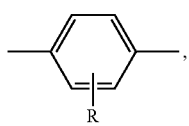

and
X and -R are as defined in regard to formula (III);
b') reacting mixture (M1) with a haloaryl compound according to formula (I) to provide a mixture (M) of mixture of dihalodiarylsulfones isomers according to formula (IIIa):

X—Ar'—SO$_2$—Ar''—X' (IIIa)

wherein
Ar' and Ar'' are aryl moieties of the formula:

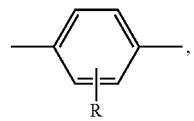

and
X, X', and R are as defined in regard to formula (III);
c') isolating 4,4'-dihalodiarylsulfone isomer from mixture (M);
d') subjecting mixture (M) from step (c') to steps a) and b) of the process of claim 1 so as to obtain a haloaryl compound according to formula (I), and
e') recycling haloaryl compound from step d') to step a') or b').

12. The process according to claim 11 wherein:
step a') is accomplished by treating the haloaryl compound with SO$_3$ at a temperature ranging from 40 to 85° C. and
step b') is accomplished at a temperature ranging from 200 to 250° C.

13. A process for manufacturing a 4,4'-dihalodiaryl sulfone according to formula (III):

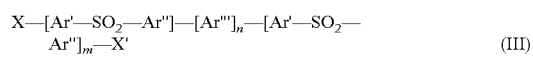 (III)

wherein
X and X' are both chlorine,
Ar' and Ar'' are both groups of the formula:

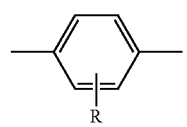

each R is independently selected from hydrogen, halogen, alkyl, aryl, ether, thioether, carboxylic acid, amine, and quaternary ammonium, and
n and m are both 0,
said process comprising:
a') chlorosulfonating a haloaryl compound according to formula (I):

X—Ar (I)

wherein
Ar is an aryl moiety of formula:

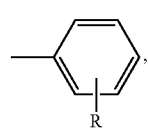

and
X and R are as defined in regard to formula (III),
to provide a mixture (M1') of haloarylsulfonyl chlorides isomers of the formula (VI):

X—Ar—SO$_2$Cl (VI)

wherein
Ar is an aryl moiety of formula:

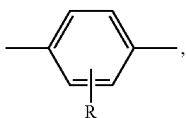

and
X and R are as defined in regard to formula (III);
b') reacting mixture (M1') with a haloaryl compound according to formula (I) to provide a mixture (M) of dihalodiarylsulfones isomers complying with formula (IIIa):

X—Ar'—SO$_2$—Ar"—X' (IIIa)

wherein:
Ar' and Ar" are aryl moieties of the formula:

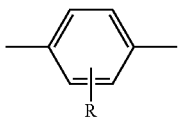

X, X', and R are as defined in regard to formula (III);
c') isolating 4,4'-dihalodiarylsulfone isomer from mixture (M);
d') subjecting mixture (M) from step c') to steps a) and b) of the process of any one of claim 1 to obtain a haloaryl compound according to formula (I), and
e') recycling haloaryl compound from step d') to step a') or b').

14. A process for manufacturing a 4,4'-dihalodiaryl sulfone according to formula (III):

X—[Ar'—SO$_2$—Ar"]—[Ar'"]$_n$—[Ar'—SO$_2$—Ar"]$_m$—X' (III)

wherein
X and X' are both chlorine,
Ar' and Ar" are both groups of the formula:

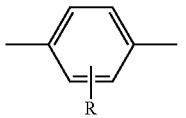

R is independently selected from hydrogen, halogen, alkyl, aryl, ether, thioether, carboxylic acid, amine, and quaternary ammonium, and
n and m are both 0, said process comprising:
a') reacting a complex of sulfur trioxide with dialkyl sulfate with a haloaryl compound according to formula (I):

X—Ar (I)

wherein
Ar is an aryl moiety of formula:

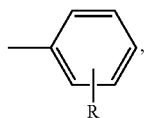

and
X and R are as defined in regard to formula (III),
to provide a mixture (M) of dihalodiarylsulfones isomers according to formula (IIIa):

X—Ar'—SO$_2$—Ar"—X' (IIIa)

wherein
Ar' and Ar" are aryl moieties of the formula:

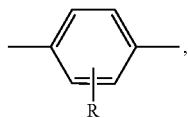

and
X, X', and R as defined in regard to formula (III);
b') isolating 4,4'-dihalodiarylsulfone isomer from mixture (M);
c') subjecting mixture (M) from step b') to steps a) and b) of the process of any one of claim 1 to obtain a haloaryl compound according to formula (I), and
e') recycling haloaryl compound from step c') to step a').

15. A process according to claim 1 wherein steps a) and b) are carried out in an equipment made of glass, silicon carbide with a content of metal silicon lower than 12%, graphite optionally impregnated with phenolic compounds, tantalum, perfluorinated polymers, or zirconium.

* * * * *